United States Patent
Naranjo Carvajal (10) Patent No.: US 7,104,681 B2
(45) Date of Patent: Sep. 12, 2006

(54) METHOD AND DEVICE TO DETERMINE THE THERMAL DIFFUSIVITY OF MATERIALS, SUCH AS THERMOPLASTIC POLYMERS, DURING NON-STATIONARY HEAT TRANSFER PROCESSES

(75) Inventor: Alberto Naranjo Carvajal, Medellin (CO)

(73) Assignee: ICIPC—Instituto De Capacitacion E Investigacion Del Plastico Y Del Caucho, Medellin (CO)

( * ) Notice: Subject to any disclaimer, the term of this patent is extended or adjusted under 35 U.S.C. 154(b) by 0 days.

(21) Appl. No.: 10/775,822

(22) Filed: Feb. 10, 2004

(65) Prior Publication Data

US 2004/0213321 A1    Oct. 28, 2004

(51) Int. Cl.
*G01K 13/00*    (2006.01)
*G01K 1/14*    (2006.01)
*G01N 25/20*    (2006.01)

(52) U.S. Cl. .................. 374/143; 374/208; 374/43
(58) Field of Classification Search ............... 374/141, 374/143, 208, 163, 43, 44; 425/542, 547, 425/552, 144, 143, 149
See application file for complete search history.

(56) References Cited

U.S. PATENT DOCUMENTS

| | | | | |
|---|---|---|---|---|
| 3,850,559 A | * | 11/1974 | Mintz et al. | 425/144 |
| 5,525,050 A | * | 6/1996 | Takizawa et al. | 425/143 |
| 2004/0115294 A1 | * | 6/2004 | Moran et al. | 425/136 |
| 2004/0251570 A1 | * | 12/2004 | Sakamoto et al. | 264/40.6 |

FOREIGN PATENT DOCUMENTS

| | | | | |
|---|---|---|---|---|
| EP | 552684 A1 | * | 7/1993 |
| JP | 56079218 A | * | 6/1981 |
| JP | 61171316 A | * | 8/1986 |
| JP | 62035819 A | * | 2/1987 |
| JP | 62035824 A | * | 2/1987 |
| JP | 05004249 A | * | 1/1993 |
| JP | 06031764 A | * | 2/1994 |
| JP | 06174553 A | * | 6/1994 |

* cited by examiner

Primary Examiner—Diego Gutierrez
Assistant Examiner—Mirellys Jagan
(74) Attorney, Agent, or Firm—Ladas and Parry LLP (57) ABSTRACT

A measurement cell for an injection machine has a cavity formed between two removable and exchangeable internal metallic blocks equipped with a cooling and heating system. The internal metallic blocks are laterally isolated from bodies that hold the blocks by a space of air that restricts transversal heat transfer in the cavity due to the presence of two polymeric bars installed on its lateral edges edges to generate a one-dimensional heat transfer regime on the central zone of a plate of material to be analyzed. The measurement cell also has a set of fixed pressure and temperature sensors on the bodies connected to a data acquisition system to store signals therefrom and a removable and reusable unit of temperature sensors that possesses ceramic or metallic tubes assembled in a block carrier to guide and fix a group of at least three temperature sensors on the cavity also connected to the same data acquisition system. The tubes are supported by bodies that enable the reuse of the plate formed as such with the temperature sensors inside to measure the heating curves when the measurement cell is operated at high temperature with its heating system.

24 Claims, 9 Drawing Sheets

METHOD AND DEVICE TO DETERMINE THE THERMAL DIFFUSIVITY OF MATERIALS, SUCH AS THERMOPLASTIC POLYMERS, DURING NON-STATIONARY HEAT TRANSFER PROCESSES

SUMMARY

Measurement cell, similar to an injection mold to manufacture a plate that can be installed on an injection molding machine, which comprises a cavity supplied with a cooling and heating system that enables to generate a one-dimensional heat transfer regime on the central zone of the plate of the material to be analyzed, a set of pressure and temperature sensors installed fixed on the mold's body and connected to a data acquisition system to store the signals, characterized because it comprises additionally a removable and reusable device called the removable Unit of temperature sensor, which allows to introduce a group of at least three temperature sensors in the cavity when the cell is open and keep them in exact positions with high precision during the cavity filling process with the melt material and during its next cooling, enabling the usage of the plate formed as such with the temperature sensors inside to measure the heating curves when the measurement Cell is operated at high temperature with its heating system.

Method to obtain, as of at least three temperature signals (triad) generated by the sensors of the removable unit of temperature sensor of the measurement Cell of this invention, curves of values of thermal diffusivity of a thermoplastic material as a function of the temperature and under the typical conditions of industrial processing of these materials characterized as well because these values of thermal diffusivity meet the discretized differential equation of a one-dimensional non-stationary heat flow by conduction.

The invention shall be described based on the figures below and an example of measurement results as follows:

DESCRIPTION

The invention comprises a Method and a measurement Cell to determine the thermal diffusivity of materials such as thermoplastic polymers during non-stationary heat transfer processes such as those of industrial processes used for its transformation into products, which can include changes of the phase of the material studied.

As it is widely known in the scientific and technical fields, the thermal diffusivity of materials like thermoplastic polymers shows significant temperature and speed dependence, with which this temperature varies during the cooling or heating processes inherent in the industrial processing of these materials in products. The values of this property are indispensable, for instance, to calculate or simulate the processing aimed at its optimization. In the case of injection molding, this value is of special importance for the reliable prediction of the cooling time, of the product's deformations and contractions, and in general, for the optimization of the mold and even the injection molding process.

Thermal diffusivity is only relevant in non-stationary heat flow processes. Therefore, its reliable measurement requires to submit the specimen to a heat transfer regime of this sort. At present, numerous experimental methods are known for said purposes. However, none of these acceptably reproduce the conditions present in the industrial processes, characterized by rapid temperature changes, even under high pressures, specially during cooling, where speeds at hundreds of Kelvin degrees per second may be present. The ranges of temperature variation obtainable in laboratory equipment are about tens of Kelvin degrees per minute.

A way to find the thermal diffusivity is to carry out experiments that enable being mathematical modeled under the supposition that thermal diffusivity remains constant in the measurement region and during the time that said measurement lasts. These experiments produce small temperature changes that serve to obtain a value of the thermal diffusivity at the temperature, almost constant, of the trial. (See for instance documents U.S. Pat. No. 5,713,665, DE19943076A1 and EP1199557A1). If diffusivity curves are desired as a function of the temperature, a trial must be made for each temperature value to thus obtain the pairs of diffusivity-temperature points required. These curves, however, are not representative of what takes place in the material during heat transfer processes under conditions of high temperature rate changes.

The other way, very disclosed in the scientific literature, is the determination of thermal diffusivity stemming from the thermal conductivity $\lambda$, the density $\rho$, and the specific heat $c_p$ at a constant pressure of the material obtained by independent methods. Thermal conductivity $\lambda$ is measured by definition under stationary heat flow conditions. Although it is possible to measure density $\rho$ under different pressure and temperature conditions, the current methods only allow maximum cooling rates of about 30 to 40 K/min. The calorimeters to determine specific heat $c_p$ solely manage cooling rates of only 40 K/mm in the best of cases and at very low pressures compared to that of industrial processes.

Independent of the method used, it is always necessary to obtain a temperature measurement inside the body. This can be obtained directly or indirectly. Indirect measurements measure any property that can be reliably correlated to the body's temperature changes in the optic birefringence of clear materials, changes in the density of the body or air that surrounds it and which generate changes in the refraction of a laser beam, for example, infrared Thermometers, etc. These methods have the advantage of being able to detect the property's change without significantly changing the temperature of the body in observation. They work well to measure temperature gradients on the bodies surface, but cannot reliably detect temperature gradients inside the body, and much less if these gradients rapidly vary during the measurement, or have spatial resolution restrictions as in the case of infrared thermometers. Direct measurements, instead, imply the presence of sensors, such as thermoelements, thermistors, resistance thermometers, etc. in contact with the material, which in some way distort the temperature to be measured, but can be used both on the body's surface as inside it keeping provided the sensor does not cross isothermal surfaces. The error of these sensors can be quantified and its readings and thermal inertia can be compensated in such a way that they can be very reliable. This belongs to the technique's stage (See documents DE 199 34 489 A1, U.S. Pat. No. 3,691,405).

The material's phase changes during the measurement give way to experimental difficulties that have not been satisfactorily resolved. Said difficulties reside in the material's expansion or contraction, which difficult guaranteeing the position of the measurement point. Moreover, the fact that the formation of crystalline structures in polymers, in the case of cooling from the molten stage, depends on the cooling conditions and that the laboratory equipment available cannot reproduce the conditions present in industrial processes is another source of enormous existing difficulties.

The general objective of the present invention is to clear away the inconveniences of the methods exposed providing a device and a method that allow the reliable determination of the thermal diffusivity of the materials exposed to rapid temperature changes, even under phase changes similar to those found in industrial processes of thermoplastic material transformation.

To clarify more the invention and its advantages compared to the techniques known, the following describes—with the help of the drawings enclosed—the possible forms to make the devices and the method to obtain thermal diffusivity of materials such as thermoplastic polymers.

Figure 1:
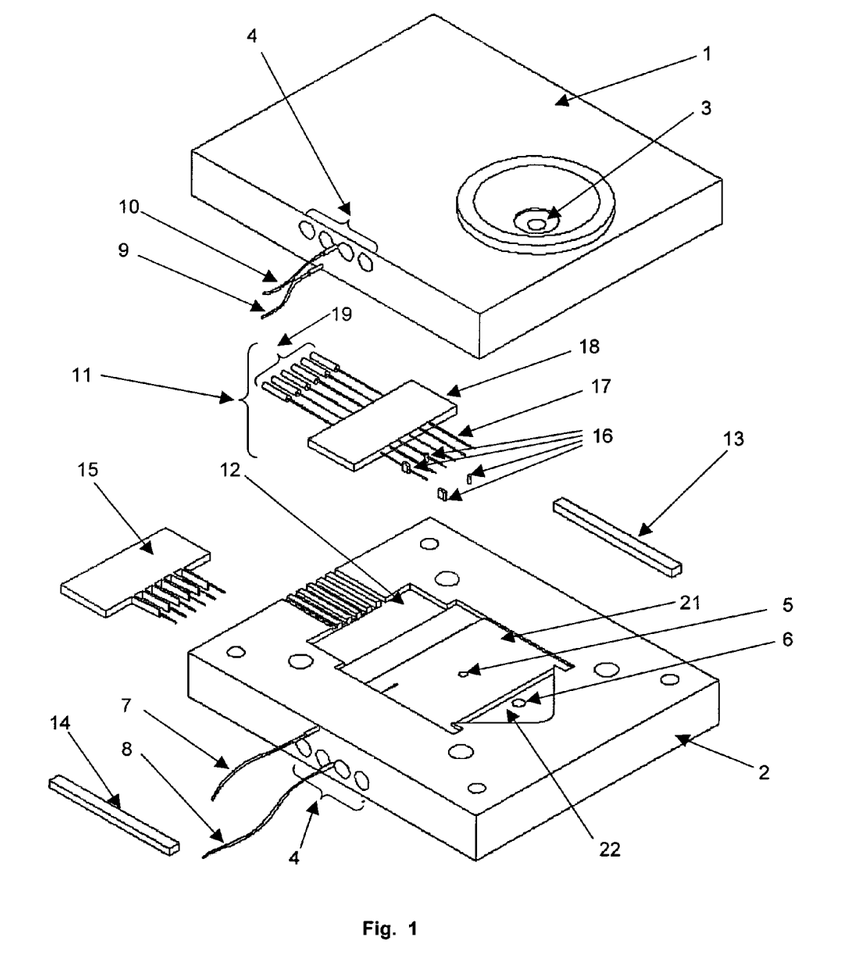
FIG. 1 schematically shows the fundamental components of the measurement cell, and the removable Unit of temperature sensors in two of the possible versions.

The measurement cell is basically composed of two symmetrical bodies 1 and 2 of FIG. 1, which are in turn composed of plates 29 and 24 that hold among them two removable and exchangeable metallic blocks 20 highly heat conductive that comprise the cavity where the material to be studied is injected through the hole 3 (omitted in FIG. 2) to the chamber 22. This chamber has a shape such that it allows the material to flow towards the cavity 21 with a flat flow front, as it can be understood by an expert of the construction technique of injection molds. The chamber 22 forms section 31 of the part in FIG. 3 and the cavity 21 the section 30 of the part called "plate" in this invention. The entrance 3 can also be located in the cell's partition line, something usual to find in injection molds. In the perforation 27 a piezoelectric sensor is installed, which serves to monitor the material's pressure during the injection. Both internal metallic blocks 20 are held between the plates that comprise the external blocks, for minimum contact and thus, minimize the heat flow outside of the internal blocks. These are isolated from the external blocks by a gap of air 23.

The figure does not represent the screws and conventional fitting elements that keep together the plates and internal blocks that comprise both symmetric bodies 1 and 2. These internal blocks are removable and exchangeable to enable the construction, to facilitate the repair of the measurement Cell, and also, so that the cavity formed among them can be achieved at different depths and thus, enable the study of diffusivity in bodies with different thickness. Both bodies should be kept joined by any device, such as a press or a closing unit of an injection machine that is capable of keeping the cell closed when the molten material to be analyzed is injected under pressure inside. The guiding elements to align both bodies during the closing and further constructive details have been omitted in the figures since these are conventional elements known by any expert in the subject of injection molds.

Figure 2:
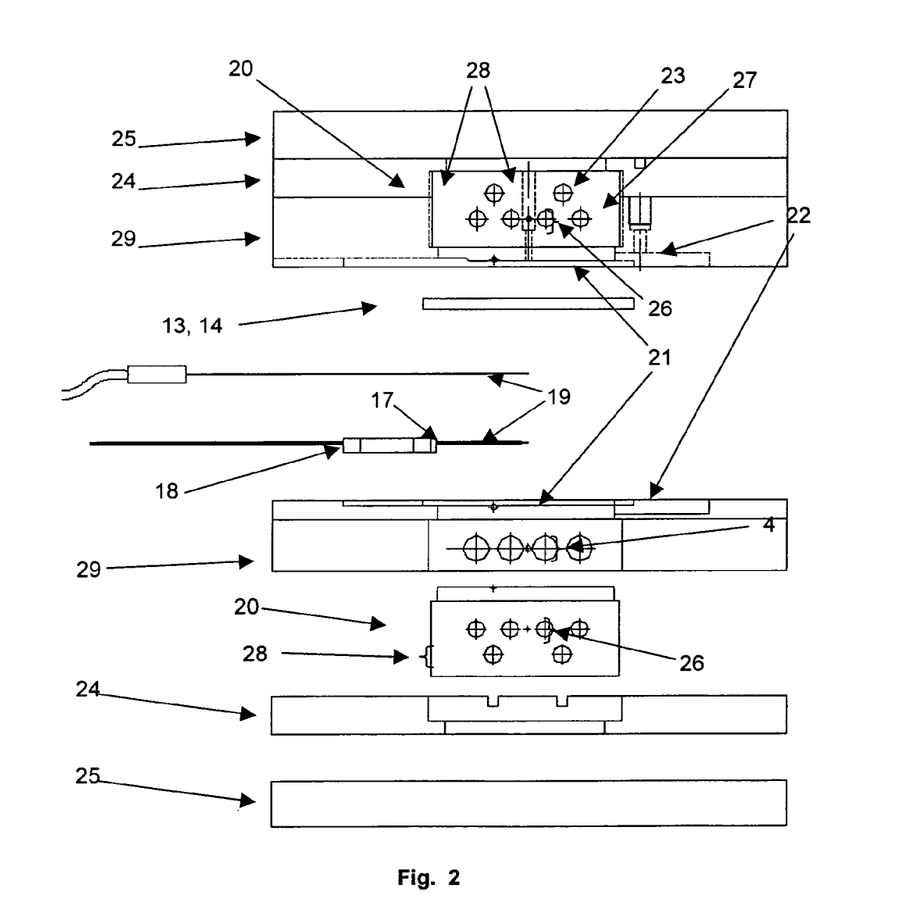
FIG. 2 shows a schematic section of the measurement cell with the body's top parts assembled.

The measurement cell is installed over the plates of insulating material 25 of FIG. 2 as that normally used in the technology of plastic injection, but with a minimum thickness of 20 mm. The conducts of the attemperator channels 26 are connected with conventional tubes (not represented in the figure) that pass without making contact through the holes 4 of FIG. 2 of the symmetrical bodies 1 and 2 to a system (not represented in the figures) that maintains a conventional attemperator liquid in circulation, like for example water or oil, at the temperature desired for the temperature of the cavity's wall of the measurement cell. The circulation system should be able to maintain the flow's temperature with a variation below ±0.5K while the cavity of the measurement cell is empty.

The pressure sensors 5 and 6 of FIG. 1 and the temperature sensors 7, 8, 9 and 10 are connected to a conventional data acquisition equipment provided of a card for analog/digital conversion preferably with a 16 bit resolution and the capacity to scan every channel at least 100 times per second. The signals of these sensors serve to supervise the conditions of the process and its stability in time. Before closing the cell, a device, called the removable Unit of temperature sensors 11, is installed inside in the space 12 provided for such purpose in the symmetrical bodies 1 and 2 of FIG. 1. The side walls of the cavity are insolated by two removable bars 13 and 14 of polymeric material.

Figure 3:
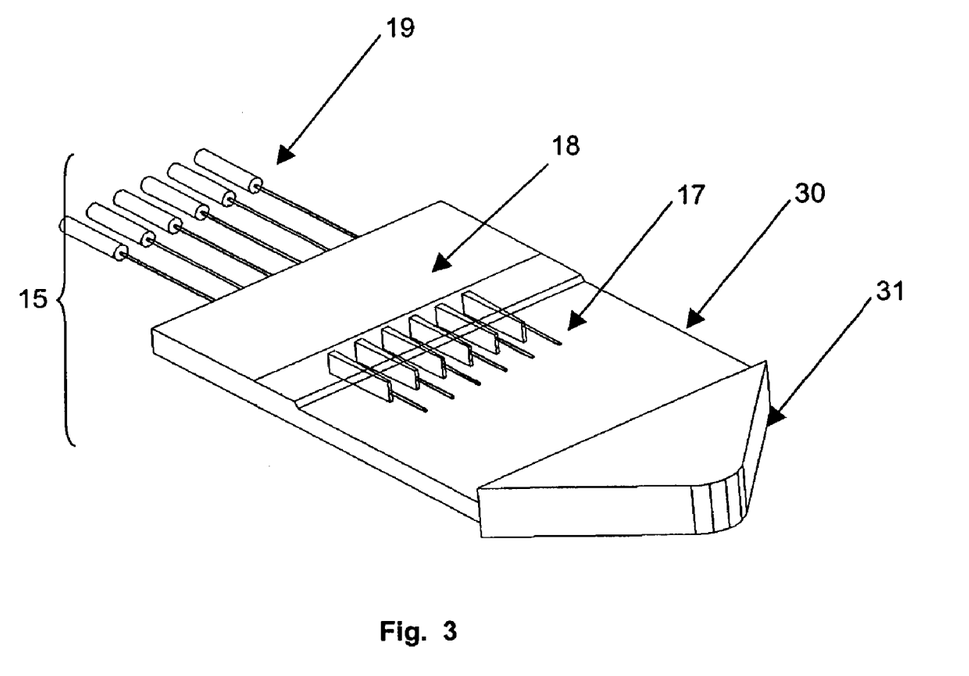
FIG. 3 schematically shows the removable Unit of temperature sensors integrated to the plate when the measurement is completed.
Figure 4:
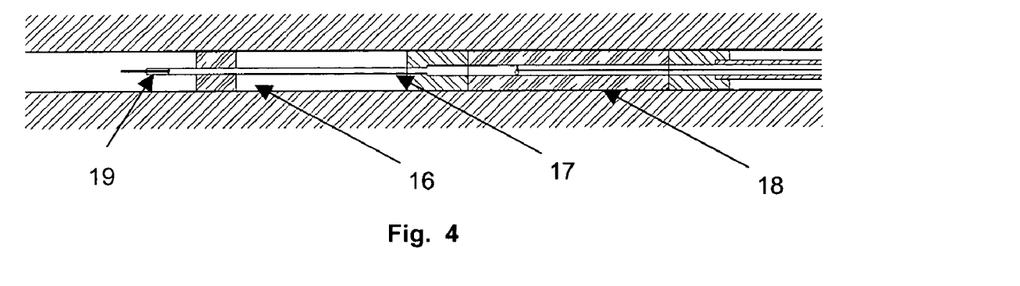
FIG. 4 shows a detail of the cylindrical tubes and their removable supports to guide and hold the temperature sensors in one of the possible variants.
Figure 5:
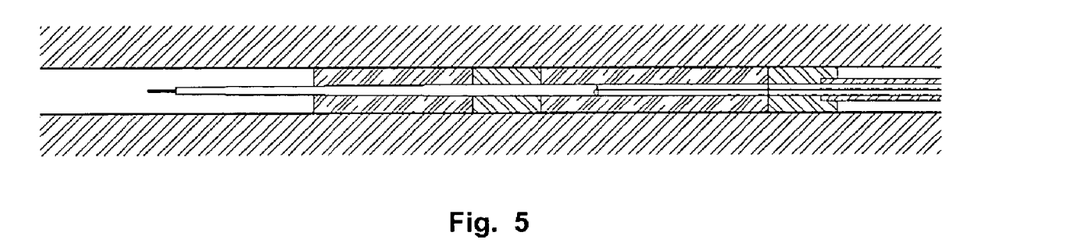
FIG. 5 shows a detail of the cone-shaped tubes and their fixed supports to guide and hold the temperature sensors in a second variant.
Figure 7:
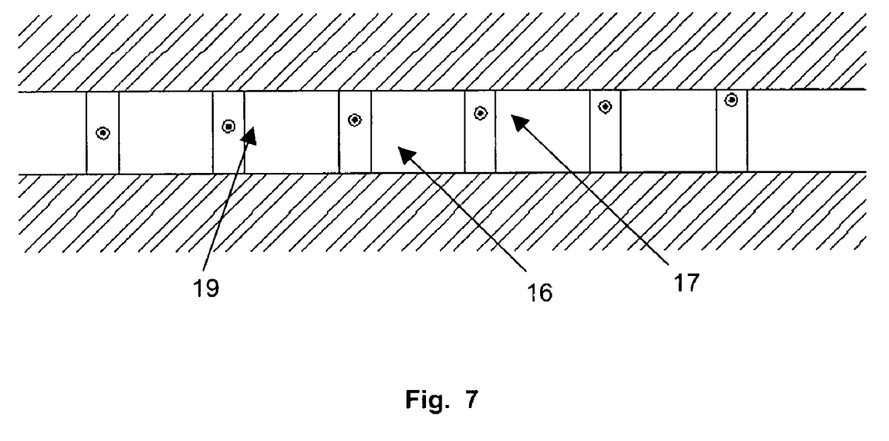
FIG. 7 shows a cross-section of the cavity at the height of the ends of the temperature sensors, which shows its distribution equally spaced upon one of the halves of the cavity's thickness of the measurement Cell.

FIG. 1 shows the removable Unit of temperature sensors 11 and its variant 15 that appears as well in FIG. 3, which is formed by a supporting block 18, which houses the tubes 17 for the insertion and fixation of the temperature sensors 19. These tubes are supported by the insolating removable positioning bodies 16 if variant 11 is used of FIG. 1 and FIG. 2. Independent of the variants used for the positioning of the temperature sensors, these always remain uniformly distributed on one of the halves of the thickness of the plate of material to be analyzed, as shown in FIG. 7. Each sensor must be calibrated and its readings must be corrected as known by any expert in temperature measurement techniques.

The measurement Cell is installed with its entrance 3 tightly coupled to a device suitable to inject the material studied in molten form, preferably an injection molding machine, which generates reproducibly the pressure and temperature needed in the material to inject it in the cavity of the measurement cell according to the modern technique of injection molding widely known.

Once the stationary thermal stage is reached in the cell, the removable unit of temperature sensors 11 or 15 is inserted in the space 12 of one of the symmetrical bodies 1 or 2; the measurement cell is closed and the recording of signals is activated to initiate the injection of the material to be analyzed. The process of signal acquisition is maintained for a time sufficient so that the material's mean temperature reaches the value desired to end the process, for example, 10K above the value set for the cavity wall of the measurement cell.

The first measurement process is carried out during the cooling of the material studied in molten stage. The temperature of the cell's cavity walls can be adjusted with the attemperator system to obtain different cooling conditions;

likewise, the melt's temperature and the injection pressure can be adjusted in order to carry out measurements under typical conditions of material processing. For this first process, the only condition needed for the temperatures is that the material is in the melt stage at the beginning and ends in the solid stage at the end of the process. The temperature data recorded are used to obtain the thermal diffusivity of the material studied during cooling.

Once the data acquisition process described in the paragraph above is completed, the cell is opened and the removable unit of temperature sensors is removed; which are now embedded on the plate of the material to be analyzed as shown in FIG. 3, whereby, for clarity purposes, the plastic plate has been drawn 30 as a clear body in the zone of the temperature sensors.

This device now integrated with the plate of the material to be analyzed is used to carry out an optional heating process, which allows to obtain the information needed to calculate the thermal diffusivity of the material during the heating, similar to that used in the heating, if so required. For that, the measurement cell is set to the desired temperature with the help of conventional electrical cartridges (not represented in the figures) installed in the perforations 28 of FIG. 2 or by flow of an attemperator liquid through the perforations 26, warmed by an attemperator not represented in the figures. Once the stationary stage is reached, the recording of signals is activated and the removable Unit of temperature sensors 11 or 15 is quickly introduced with the temperature sensors embedded on the plate of the material to be analyzed, and the measurement cell is closed.

The signals acquisition process is extended to the time needed so that the final mean temperature of the plate differs little, for example 5K, from the temperature chosen for the cavity's walls. The recorded temperature data are used to obtain the thermal diffusivity of the material studied during the heating.

To extract the device 11 or 15 which fixes the temperature sensors of the plate 30 of the material to be analyzed, the plate's temperature should be at least 5K below the temperature of the solidification of the material to be analyzed. In this stage, the plate can be removed from the fixation device of the temperature sensors, pulling it carefully axially from said sensors.

Figure 8:
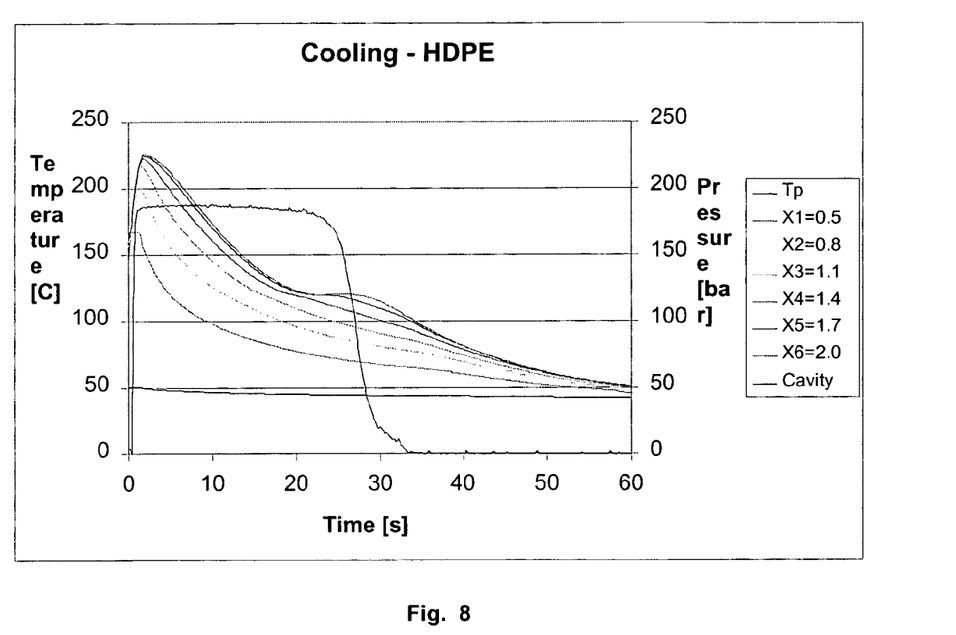
FIG. 8 shows an example of the temperature curves obtained in a measurement.

An example of the measurements results is shown in FIG. 8, where 6 internal temperatures are recorded as well as those of the cavity during a high density polyethylene cooling experiment, for a plate 4 mm thick, cooled from 230° C. to approximately 50° C., with a cavity wall temperature adjusted in stationary regime at 40° C. For the experiment, a removable Unit of temperature sensors was used as represented in 15 of FIG. 1, with 6 temperature sensors spaced 6 mm among each other. The sensor closest to the wall is at 0.50±0.01 mm and the sensor farthest is in the center of the cavity's height. The increment of these distances is constant and equal to 0.30±0.01 mm. These curves were stored every 0.2s and converted to digital values with a resolution of 0.06° C. in a data acquisition system set to the specifications given in the present invention. Once the curves were obtained, they were corrected according to the calibration values obtained for each temperature sensor of the removable unit according to the techniques known for these measurement tasks. Table 1 shows the structure required in the data to enable their analysis according to Eq. 1.

TABLE 1

| Time | ... | Temp. in Position i−'1 | Temp. in Position i | Temp. in Position i + 1 | ... | Cavity Pressure | Chamber Pressure |
|---|---|---|---|---|---|---|---|
| ... | | | | | | | |
| 11.40 | | 150.28 | 159.52 | 165.25 | ... | 184.6 | 178.0 |
| 11.60 | ... | ... | 158.29 | ... | ... | | |
| ... | | | | | | | |

Figure 9:
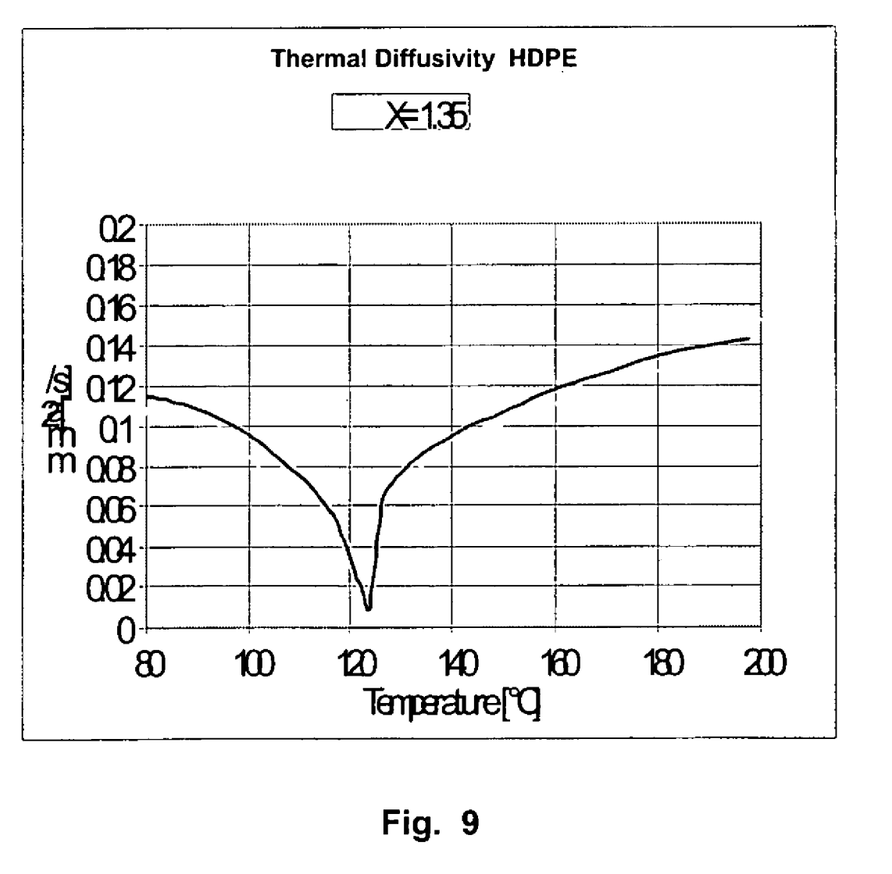
FIG. 9 shows an example of the thermal diffusivity curve for a thermoplastic material obtained with the method and the cell of this invention.

The value of the diffusivity obtained for the interval's mean temperature (158.91° C.) and at a mean pressure (Cavity Pressure) of 182.3 bar is of 0.11 mm²/s. This repeats itself on every line of the data file. For the final presentation of the diffusivity curve, the values obtained are approximated, according to the usual numeric techniques, to a smooth line with a lower quadratic error. FIG. 9 shows an example of the curve for thermal diffusivity obtained from a triad of data with the central sensor in a position at 1.35 mm of the closest wall. The six temperature curves of the example enable to form 4 groups of three of adjacent temperatures to obtain other curves of thermal diffusivity for the prevailing conditions in each of the central sensor of the corresponding groups of three.

$$a(X_i, \vartheta_{i,j}, \vartheta_{i,j}, p) = \frac{\vartheta_{i,j+1} - \vartheta_{i,j}}{\vartheta_{i+1,j} + \vartheta_{i-1,j} - 2\vartheta_{i,j}} \cdot \frac{\Delta x^2}{\Delta t} \qquad \text{Eq. 1}$$

x=Separation between temperature sensor of the triad and measured in the heat flow direction t=Time difference between values taken of the temperature curves θi,j=Temperature for position $X_i$ in time j (central temperature of the triad)

$\theta_{i,j}$+1=Temperature for position $X_i$ in time j+t (central temperature of the triad)

$\theta_{i+1,j}$=Temperature for position $X_{i+1}$ in time j (temperature for the point of the triad farthest away from the cavity's wall)

$\theta_{i-1,j}$=Temperature for position $X_{i-1}$ in time j (temperature for the point of the triad closest to the cavity's wall)

Figure 6:
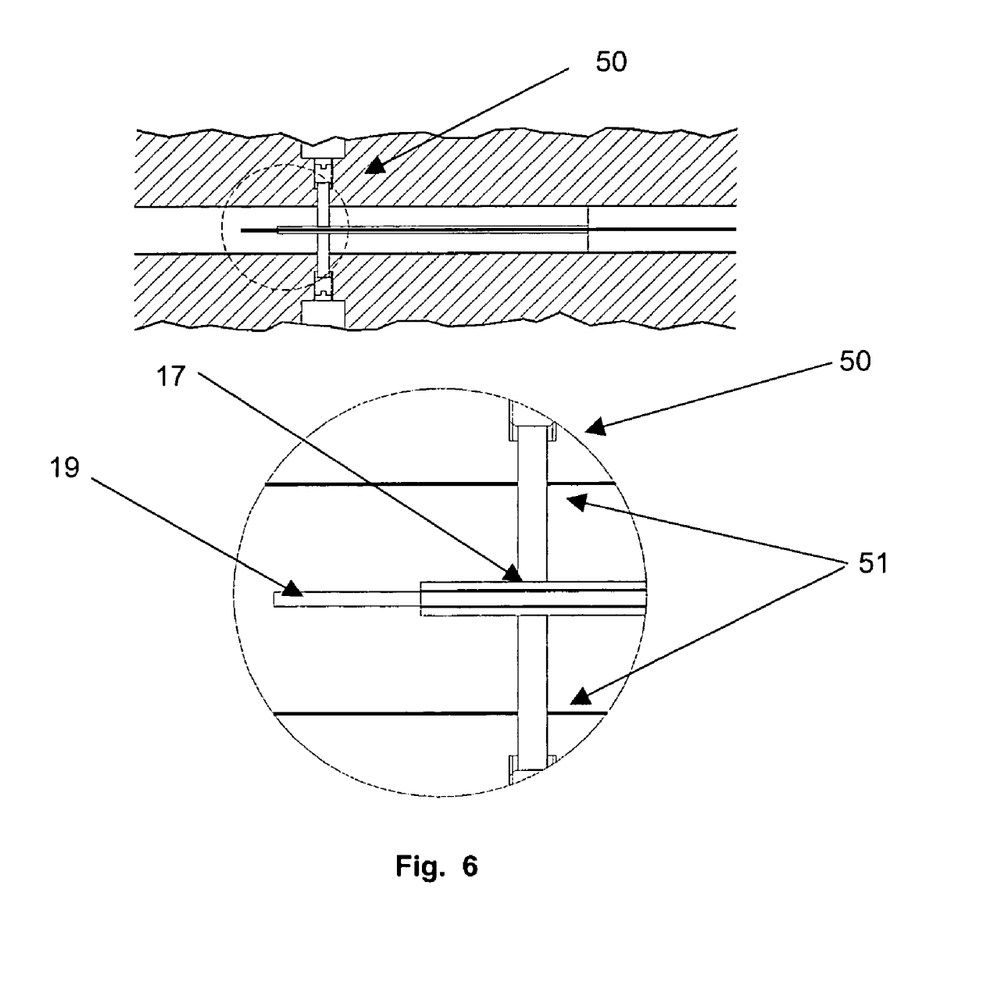
FIG. 6 shows a detail of the tubes and their supports to guide and hold the temperature sensors in a third variant.

Naturally, the realization options explained above are not the only ones possible and consequently, should not be taken as a limitation of the claims. In FIG. 6 it can be seen for example, another option to set the temperature sensors, which consists of a pair of cylinders 51 adjustable by the threaded section 50 in the positions required by the sensor. The values of the separation of the sensors among themselves and regarding the cavity wall are also values of example and should not be considered as sole possibilities. The thickness of the plate can also be achieved by methods other than changing the blocks 20, as could be for instance the usage of plates or supplements over these blocks or any other system of general domain among the experts of injection mold construction.

The invention claimed is:

1. Measurement cell for an injection machine, the measurement cell comprising:

a cavity between two removable and exchangeable internal metallic blocks each having a cooling and heating system and being isolated from bodies that hold the blocks by both a space and polymeric bars to generate a one-dimensional heat transfer regime for a central zone of a plate of material to be analyzed;

a set of fixed pressure and temperature sensors on the bodies for connection to a data acquisition system to store signals therefrom; and a removable and reusable unit of at least three temperature sensors for connection to the data acquisition system, the temperature sensors being in ceramic or metallic tubes in a supporting block to guide and fix the unit at the cavity.

2. Measurement cell according to claim 1, wherein the removable and exchangeable internal metallic blocks have a thermal conductivity higher than 100 times that of the material to be analyzed.

3. Measurement cell according to claim 1, wherein the space is at least 1 mm thick.

4. Measurement cell according to claim 1, and further comprising a chamber between the metallic blocks that produces a flat flow front of the material to be analyzed as being fed into the cavity.

5. Measurement cell according to claim 1, wherein the chamber has a minimum depth of 2.5 times a thickness of the cavity.

6. Measurement cell according to claim 1, wherein a distance of the temperature sensors from a face of the unit closest to the cavity varies less than 0.5%.

7. Measurement cell according to claim 1, characterized because the removable unit of temperature sensors is reusable for other measurements.

8. Measurement cell according to claim 1, characterized because the removable unit of temperature sensors allows to replace the temperature sensors in case these are damaged.

9. Measurement cell according to claim 1, wherein the ceramic or metallic tubes have an external diameter in a zone at the temperature sensors not above 2.4 times the diameter of the temperature sensors.

10. Measurement cell according to claim 1, characterized because the removable unit of temperature sensors possesses ceramic or metallic tubes assembled in a carrier block manufactured in a polymeric or ceramic material with enough mechanical resistance to support the pressure during the usage of the measurement cell.

11. Measurement cell according to claim 1, wherein the removable unit of temperatures sensors possesses ceramic or metallic tubes supported on integrated or removable bodies made of ceramic, polymeric or wood material whose resistance to compression is above minimum 2 times the maximum compression effort generated during the closing of the measurement cell.

12. Measurement cell according to claim 1 characterized because the removable unit of temperature sensors possesses ceramic or metallic tubes that can be supported on integrated bodies made of ceramic or polymeric material whose height is higher than the cavity's height without exceeding it by 1% and whose thickness is not above 1.5 mm.

13. Measurement cell according to claim 1, wherein lengths of the ceramic or metallic tubes inside the blocks is not below 40 times the diameter of the temperature sensors.

14. A measurement cell for measuring thermal diffusivity of materials during a non stationary heat transfer process, that can be installed, opened and firmly closed in an injection molding machine comprising:

a flat and narrow cavity for a material whose thermal diffusivity is to be measured;

two removable and exchangeable metallic blocks that form two rectangular and opposite big faces of said cavity, equipped with a cooling and a heating system that guarantee a one dimensional heat flow in said cavity by the presence of an isolating film of air;

two polymeric bars forming two opposite narrow faces of said cavity that restrict the transversal heat flow in said cavity;

a removable unit of temperature sensors located at a third, narrow face of said cavity, made of an isolating material that has ceramic or metallic small tubes embedded in a supporting block to guide and fix a group of temperature sensors extended into the central zone of said cavity connected to a data acquisition system to store their temperature signals; said tubes are fixed by small rips of said supporting block or by removable and reusable fixing elements that hold the temperature sensors in their exact position inside said cavity;

a chamber coupled with said cavity to a fourth, narrow face;

two pressure sensors, one located in said cavity and the second one in said chamber, connected to said data acquisition system to store their pressure signals; and two temperature sensors lying on the two rectangular and opposite big faces of said cavity.

15. The measurement cell of claim 14 in which the said two removable and exchangeable metallic blocks have drilled through holes parallel to the surfaces forming the two big flat faces of said cavity, where the holes closest to the said cavity faces are for the flow of a cooling liquid, and those far away from the cavity faces are for conventional high watt density cartridge heaters.

16. The measurement cell of claim 14 in which one of the said two removable and exchangeable metallic blocks has a mini pressure sensor of a diameter no larger than 2.5 mm installed and located on the central zone of said cavity, where the material temperature is measured.

17. The measurement cell of claim 14 in which the said two polymeric material bars are removable and made of a polymer that does not melt at the maximum temperature of said heat transfer process.

18. The measurement cell of claim 14 in which said removable unit of temperature sensors can be easily fixed and exactly installed on the third narrow face of said cavity.

19. The measurement cell of claim 14 in which said removable unit of temperature sensors has temperature sensors exactly and stable positioned in pre-established distances from the closest face of said cavity and parallel to it with an accuracy below 0.5% of the said distance during the entire time of said heat transfer process.

20. The measurement cell of claim 14 in which said removable unit of temperature sensors allows the installation of minimum three temperature sensors.

21. The measurement cell of claim 14 in which said removable unit of temperature sensors has small cylindrical or conical ceramic or metallic tubes to guide the said temperature sensors.

22. The measurement cell of claim 14 in which the said supporting block of said removable unit of temperature sensors is manufactured in a polymeric or ceramic material with enough mechanical resistance to support the internal cavity pressure during the said measurement.

23. The measurement cell of claim 14 in which said ceramic or metallic tubes are fixed by small rips of said supporting block or by removable and reusable fixing elements made of ceramic, polymeric or wood with a compression resistance of minimum 2 times the maximum compression stress generated when said measurement cell is closed.

24. The measurement cell of claim 14 in which the height of said small rips or removable and reusable fixing elements is up to 1% higher than the cavity's height and its thickness is not above than 1.5 mm.

* * * * *